United States Patent
Matsuo et al.

(10) Patent No.: US 7,354,608 B1
(45) Date of Patent: Apr. 8, 2008

(54) BIO-IDENTICAL HORMONES AND METHOD OF USE

(75) Inventors: Susan Matsuo, 550 Elm Way, #408, Edmonds, WA (US) 98020; Teresa Leigh Barr, Hood River, OR (US)

(73) Assignee: Susan Matsuo, Edmonds, WA (US)

( * ) Notice: Subject to any disclaimer, the term of this patent is extended or adjusted under 35 U.S.C. 154(b) by 367 days.

(21) Appl. No.: 11/145,856

(22) Filed: Jun. 6, 2005

Related U.S. Application Data

(63) Continuation of application No. 10/246,358, filed on Sep. 18, 2002, now Pat. No. 6,967,194.

(51) Int. Cl.
*A61K 36/258* (2006.01)

(52) U.S. Cl. .................. 424/728; 424/198.1; 514/169; 514/171; 514/184; 514/505

(58) Field of Classification Search ............... 424/728, 424/198.1; 514/169, 171, 184, 505
See application file for complete search history.

(56) References Cited

U.S. PATENT DOCUMENTS 6,967,194 B1 * 11/2005 Matsuo et al. .............. 514/171

* cited by examiner

*Primary Examiner*—Herbert J. Lilling
(74) *Attorney, Agent, or Firm*—Buskop Law Group, PC; Wendy Buskop

(57) ABSTRACT

The embodied composition is an evening dose of bio-identical hormones in a solvent with a vasodilator, a hormone modulator, and a carrier for balancing and maintaining Cortisol level in a human. The evening dose comprises progesterone ranging from 0.005 wt % to 41 wt %; pregnenolone ranging from 0.005 wt % to 41 wt %; ethoxydiglycol ranging from 0.005 wt % to 10 wt %; pentoxifylline ranging from 0.005 wt % to 10 wt %; ginseng ranging from 0.005 wt % to 41 wt %, and carrier q.s. Embodied herein is a method for balancing and maintaining Cortisol levels in humans by identifying the hormonal needs for a human, testing to ascertain the current relationship between of hormone levels, inserting the values of each hormone level into a hormone tree, balancing the hormones to a normal level, adjusting the levels for symptoms and sex type, and forming a resultant composition.

6 Claims, No Drawings

BIO-IDENTICAL HORMONES AND METHOD OF USE

CROSS REFERENCE TO RELATED APPLICATIONS

The present application is a Continuation to U.S. patent application Ser. No. 10/246,358 filed on Sep. 18, 2002 now U.S. Pat. No. 6,967,194, entitled "Bio-Identical Hormones and Method of Use".

FIELD

The present embodiments take the concept of bio-identical hormone replacement out of the mentality that associates hormones only with sexuality. The present embodiments encompass both nighttime and morning formulas to maintain optimal health for humans and animals.

BACKGROUND

While hormones determine sexual gender and developmental characteristics, they also fine-tune a person's capability to function optimally in the body and mind. Viewing the list of possible problems associated with hormone imbalance, it is clear that the effects are broad and far-reaching. They encompass all body/mind systems. They are integral for maintaining health and wellbeing. The present invention encompasses both nighttime and morning formulas to maintain optimal health for humans and animals.

The present embodiments utilize hormones to play a vital role in maintaining Cortisol levels involved in good cognitive function such as memory. Studies indicate hormones may protect both men and women from cardiovascular disease. Many find that when hormones are balanced naturally and individually, they have less stress, more energy and have a feeling of wellbeing. Bio-identical hormones are hormones that are: bio-identical to what humans naturally produce or produced at one time in their lives, can be naturally made from plant sources or of pharmaceutical quality and therefore bio-available. The present embodiments utilize all types of hormones within its concepts.

Correct individual hormone balance is the key to the present invention as well as determining the correct dosage of each hormone. Each person is different in his or her requirements. Hormonal needs vary dramatically from one individual to the next. Each individual's hormones fluctuate depending on changing levels of stress as well as other life events. It is important to fine-tune hormone replacement and learn how to listen to a body's hormone needs. Too much or too little will both lead to hormone imbalance. Optimum feelings of wellness come from the 'correct individual balance'. One can think of hormone balance as a teeter-totter, where if one section is out of synchronization, one side is too high and the other is too low.

All hormones are found in both men and women. Each sex has more of some and less of others. Sexual gender and an individual's genes determine this ratio. Considering genetic history is important. The present invention uses the following diagram to describe hormone balance as a hormonal tree. All hormones are derived from cholesterol.

The following paragraphs discuss some of the chemicals associated with this invention.

Andrestenediol or Androdiol ($C_{20}H_{32}O_2$) is also known as 4-AD, 4-androstenediol, or 5-androstendiol. The scientific names for Andrestenediol include 4-androstenone-3beta, 17 beta-diol and 5-androstene-3beta, 17 beta-diol. Mechanism of action in the body: there is evidence that exogenous androstenediol is converted to testosterone in humans. One use of Andrestenediol is to increase endogenous testosterone in humans; it is a precursor hormone to testosterone and estrogen. Andrestenediol can be purchased from LPJ Research, Inc., 352 Promontory Drive West, Newport Beach, Calif., 92660, 949-566-9841.

Androstenedione ($C_{19}H_{26}O_2$) is also known as Andro and Androstene. The scientific names are 4-androstene-3, 17-dione; and androst-4-ene 3, 17-dione. Androstenedione's mechanism of action is as a steroid hormone produced by the adrenal glands, testes and ovaries. It is a direct precursor of testosterone and estrogen in both men and women. Androstenedione production peaks in the mid-twenties and declines steadily after the age of 30. It has been used to improve athletic performance and to build muscle. Androstenedione raises DHEA levels and also raises estrogen levels. Andestrenedione can be purchased from Hawkins, 3000 East Hennepin Avenue, Building 7, Department PH, Minneapolis, Minn., 55413, 800-375-0009.

Cortisol is the primary glucocorticoid produced by the adrenal cortex gland. Ninety percent of the Cortisol secreted in circulation is bound to protein, mainly to Cortisol-binding globulin. Cortisol is a steroid hormone that is released from the zona fasciculata of the adrenal cortex in response to stress. Some of the stressors that stimulate release of this glucocorticoid hormone include drastic changes in temperature, or heavy exercising. Cortisol is considered such a reliable indicator of stress upon a system that many physiologists define stress as an event that elicits increased levels of Cortisol. The release of Cortisol begins with the hypothalamus. The hypothalamus receives input about stressors affecting the system and transfers this information in through a chemical called corticotrophin-releasing hormone (CRH). CRH travels through a portal vessel to the anterior pituitary gland where it stimulates the release of adrenocorticotrophic hormone (ACTH). The ACTH then circulates to the adrenal cortex where it stimulates the production and release of Cortisol. Once secreted into the general circulation Cortisol inhibits the release of CRH and also inhibits sensitivity to CRH thereby establishing a negative-feedback control over the system. The actual effect of Cortisol on an organism is to alter metabolic functioning and the body's immune response. Increased Cortisol levels alter organic metabolism in a number of ways. It results in an increased mobilization of amino acids from protein stores in extra hepatic (non-liver) cells. It also results in an increase in transport of these amino acids to the liver. The liver converts these amino acids to glucose through a process called gluconeogenesis and uses the amino acids to increase production of plasma proteins. The increase in Cortisol levels also serves to mobilize fatty acids from adipose tissues in an attempt to shift cells in the metabolic systems from the utilization of glucose for energy and to the utilization of fatty acids instead. In addition to its metabolic function, increased levels of Cortisol serve to suppress the immune system. Increased levels of Cortisol serve to decrease the production of lymphocytes and antibodies. Suppressing the immune system may be helpful in reducing some damaging effects of an immune response. The action of Cortisol has many significant medical implications. Cortisol could be used for diabetics who may require more insulin when they are under stress to cope with the increase blood glucose levels. Surgeons must be aware that their patient's protein catabolism may increase due to the stressfulness of their situation, which could be treated with Cortisol. Cortisol's ability to suppress the immune response may be exploited clinically to treat various inflammatory conditions such as allergies and arthritis. Cortisol may also be used in organ transplant operations to reduce the chance of organ rejection. Cortisol helps an organism cope more efficiently in its environment. Cortisol is important in glucose and energy balance as well as moderating inflammatory response and immune mechanisms, in addition to many other functions. Cortisol is a hormone for controlling stress.

The body's level of Cortisol in the bloodstream displays a diurnal variation, that is, normal concentrations of Cortisol vary throughout a 24-hour period. Cortisol levels in normal individuals are highest in the early morning around 6:00-8:00 am, and are lowest around midnight. Normal levels of Cortisol in the bloodstream range from 6-23 mcg/dl (micrograms per deciliter). In addition to early morning, Cortisol levels may be somewhat higher after meals. The most commonly used test is a measurement of the Cortisol level in the blood, although some doctors measure Cortisol through a saliva sample. Salivary Cortisol levels have been shown to be a good index of blood Cortisol levels. Occasionally by-products of Cortisol metabolism are also measured, such as 17-hydroxycorticosteroids, which are the inactive products of Cortisol breakdown in the liver. In some cases measurement of urinary Cortisol levels is also of value. For this test, urine is collected over a 24-hour period and analyzed. Normal 24-hour urinary Cortisol levels range from 10-100 micrograms/24 hours.

Dehydroepiandrosterone ($C_{19}H_{28}O_2$) is also known as DHEA, GL 701, or Prasterone. The scientific names include Dehydroepiandrosterone and Prasterone. DHEA's mechanism of action: it is endogenously produced in the adrenal glands and the liver of humans. DHEA is a sulfate ester, dehydroepiandrosterone sulfate (DHEA-S) and DHEA are inconvertible. DHEA is initially converted to DHEA-S, which is considered the storage form of DHEA. Peripheral tissues and target organs convert DHEA-S back to DHEA, which is then metabolized into androstenedione, the major human precursor to androgens and estrogens. DHEA and DHEA-S levels are higher in men, and naturally decline with age in both sexes. Because of this decline, it is suggested that replacing DHEA through supplementation might improve the outcome of diseases and conditions associated with aging. DHEA can be purchased from Hawkins, 3000 East Hennepin Avenue, Building 7, Department PH, Minneapolis, Minn., 55413, 800-375-0009.

Estradiol ($C_{18}H_{22}O_2$) is a potent mammalian estrogenic hormone produced by the ovary. It triggers the production of gonadrotropins leading to ovulation. Estradiol has been isolated from the follicular fluid of sow ovaries, and from the urine of pregnant women and mares. It makes up 10%-20% of the estrogen in younger women. Estradiol is thought to be important to protect cardiovascular and cognitive function.

Estrogen is primarily a female sex hormone, and is responsible for the growth of female sexual characteristics and female reproductive functions. Estrogen is made in the ovaries as well as fat cells, muscle cells and skin. Estrogen is produced before and after menopause.

Estrone makes up 10%-20% of the total estrogen in younger women. Also, it is made in both female and male fat cells, as well as muscle cells. This compound is very potent and it can cause cells to divide.

Pregnenolone's ($C_{21}H_{32}O_2$) scientific names include Pregnenolone; (3 beta)-3 hyroxypregn-5-en-20-one; delta 5-pregnen-3 beta-ol-20-one; and 17 beta-(1-ketoethyl)-delta 5 androsten-3 beta-ol. The mechanism of action of pregnenolone is that it is produced by the body from cholesterol and it is the precursor for all the steroid hormones, including progesterone, aldosterone, Cortisol, DHEA, testosterone, and estrogens. Low cerebrospinal fluids levels of pregnenolone are reported in people with affective disorders particularly during episodes of active depression. Pregnenolone has antagonist activity at GABA-A receptors in the brain and induces changes in the sleep EEG by increasing the time spent in slow wave sleep. Sometimes pregnenolone is called the "mother" of all hormones. It is the first hormone made from cholesterol and is the precursor of all the rest of the hormones in the hormone tree, see diagram 3. In other words, wherever there is a deficiency in the hormone tree, pregnenolone can be converted into that hormone to correct the imbalance. Pregnenolone can be purchased from, Hawkins, 3000 East Hennepin Avenue, Building 7, Department PH, Minneapolis, Minn., 55413, 800-375-0009.

Progesterone ($C_{21}H_{30}O_2$) is also known as Corpus luteum hormone, luteal hormone, luteohormone, lutine, NSC-9704, pregnancy hormone, pregnanedione, progestational hormone, or progesteronum. The scientific names are progesterone, 4-pregnene-3, and 20-dione. The mechanism of action for progesterone is an endogenous progestin secreted by the corpus luteum. It is primarily secreted during the luteal phase of the menstrual cycle, but small amounts are also secreted during the follicular stage. The normal physiological effects of progesterone are responsible for its therapeutic benefit when administered exogenously. Metabolites of progesterone have been found to have sedative-hypnotic properties and a precursor to most sexual hormones. Progesterone functions to help with sleep and reduce stress. Progesterone also decreases the size of an enlarged prostate, and is good for the bones of both males and females. Studies call it a "bone tropic hormone", as it helps to build bone. Progesterone levels may become deficient at 25-30 years of age. This deficiency affects fifty percent of women by age 35 in the United States, thus creating estrogen dominance. Source: pg. 233 "WHAT YOUR DOCTOR MAY NOT TELL YOU ABOUT PRE-MENOPAUSE", Jesse Hanley, Md.

Progesterone may help with emotional and psychological symptoms, libido, headache, rhinitis, sore throat, sinusitis, skin dryness, alopecia (thinning hair), glaucoma, and auto-immune disorders. It may improve a lipid profile, cause new bone formation, decrease risk of coronary vasospasms, and is often effective for pre-menstrual syndrome. Progesterone can be purchased from, Hawkins, 3000 East Hennepin Avenue, Building 7, Department PH, Minneapolis, Minn., 55413, 800-375-0009.

A woman may begin to show signs and symptoms of estrogen dominance. This can occur in one of two ways, the first is that the woman possesses a naturally high level of estrogen. This can be an individual genetic difference, or a combination of a genetic difference with being overweight or having substantial muscle mass. In a varying degree in all women, fat cells, muscle cells and skin cells can make estrogen. The amount of estrogen made by these cells is genetically pre-determined. That is why the amount of bio-identical progesterone necessary to balance estrogen dominance or the estrogen dominant syndrome varies from individual to individual.

Estrogen dominant symptoms include weight gain (a conversion of food energy into stagnant energy), water retention, a craving for carbohydrates, oversensitivity, irritability, insomnia, acceleration of the aging process, allergy symptoms, asthma, hives, rash, sinus congestion, dry eyes, auto-immune disorders, headaches, cold hands and feet, fatigue, fibrocystic breasts, foggy thinking, lethargy, depression with anxiety symptoms, vaginal dryness, hot flashes, irregular menstrual cycle, decreased libido, cervical dysphasia, infertility, breast cancer, osteoporosis, mood swings, uterine fibroids, zinc deficiency, breast tenderness, thyroid dysfunction resembling hypothyroidism, polycystic ovaries, PMS, memory loss, magnesium deficiency, hair loss, endometrial cancer, and copper levels in excess.

Estrogen deficiency symptoms include vaginal dryness, problems with memory, hot flashes, night sweats, depression, lethargy, and fatigue.

Note that many symptoms can be addressed first with bio-identical progesterone, and then it is necessary to add bio-identical estrogen. Bio-identical progesterone appears (at least in literature that does not come from drug companies) to be a safe choice in terms of cancer risks. It is recommended to start with bio-identical progesterone and then add bio-identical estrogens. The present invention relates to personal hormone balance, adjustable to individual needs for humans and animals. Those needs are determined by individual wellness.

Men may show signs of estrogen dominance such as prostate cancer, irritability, water retention or bloating, thyroid dysfunction resembling hypothyroidism, sluggish metabolism, enlarged prostate, depression, insomnia, anxiety, irritability, and mood changes.

Men may show signs of progesterone deficiency such as enlarged prostate, depression, insomnia, anxiety, irritability, and mood changes.

Men may show testosterone deficiency signs such as poor memory, changes in libido and potency, lower energy levels, weakness, low confidence, passivity, early senility, inner tension, mental sluggishness, poor concentration, fatigue, and hypochondria.

Women who have progesterone deficiency may show signs such as weight gain, hot flashes, sleeplessness, hypothyroidism, yeast infections, and fibrocystic breasts.

Young women with PMS syndrome, mood swings, endometriosis, fibrocystic breasts, uterine fibroids, water retention and bloating, infertility, and premenstrual headaches could be helped with the present invention.

Older women with the symptoms of anxiety, osteoporosis, midlife weight gain, hot flashes, insomnia, mid life depression, midlife onset allergies, sinusitis, rhinitis, sore throat, fatigue, weakness, dry or coarse skin and hair, hair loss, cold hands and feet, poor libido, glaucoma, normalized blood sugar, and immune deficiencies could also be helped.

Pre-menopausal progesterone deficiency symptoms such as endometriosis, infertility, uterine fibroids, fibrocystic breasts, PMS, yeast infection, insomnia, mood changes, fatigue, and mild depression could be helped.

The present invention looks at the lists of excess and/or deficiency signs and determines individual needs. The more signs and symptoms that are experienced the greater the imbalance. All humans and animals are very different from each other, so the present invention must be adjustable to each individual need. Some people are very sensitive to hormones even with a lot of symptoms and may only need a little amount replaced. Others may have only a few symptoms but may require much larger doses to have effect. Still others may show no signs or symptoms but may be suffering from deficiencies that would benefit from bio-identical hormone replacement.

There are times when a good maintenance balance is achieved and the dosage needs adjustment. For example, when one is under a lot of stress they may want to increase the bio-identical progesterone dose. This would be true for both men and women. When under stress humans and animals produce Cortisol from progesterone and decrease the amount of Progesterone available in their bodies.

There are body mass differences that need to be considered when contemplating hormone dosage. Muscle cells, fat cells and skin cells can make estrogen. How much estrogen they produce genetically pre-determined. For example, a person that is 25-30 pounds overweight definitely has more estrogen than he or she would if they of normal weight. However, another person may be 50-60 pounds overweight but their fat cells may produce less estrogen than the person who is 25-30 pounds overweight due to a difference in genetics.

A woman may work out 3-4 days a week and have some muscle mass but still be on the lean end of the continuum and have high natural estrogen levels produced in her muscle cells. She could have higher levels of estrogen than someone 25-30 pounds overweight who has a less active fat/body mass in terms of producing estrogen.

Stress is another factor that influences our hormone levels. The adrenal cortex produces Cortisol in response to stress. The Cortisol is made from progesterone.

Other compounds integral to the present embodiments are discussed in the following paragraphs.

Ethoxy Diglycol ($C_6H_{14}O_3$) is a liquid solvent prepared from ethylene oxide, a petroleum product. It is used as a solvent and thinner in preparations. The compound absorbs water and is non-irritating to human skin.

Pentoxifylline is a methylxanthine derivative that increases blood flow by decreasing blood viscosity. Pentoxifylline ($C_{13}H_{18}N_4O_3$) is also known as 3,7, dihydro-3,7-di-methyl-1-(5-oxohexyl)-1H-purinr-2,6-dione.

Estriol ($C_{18}H_{24}O_3$) is metabolite of, and considerably less potent than, the hormone estradiol. Estriol is usually the predominant estrogenic metabolite found in urine. During pregnancy the placenta produces large amounts of estriol. Isolated from human urine during pregnancy it probably occurs as a gycuronide. Estriol can be purchased from, Hawkins, 3000 East Hennepin Avenue, Building 7, Department PH, Minneapolis, Minn., 55413, 800-375-0009.

Siberian Ginseng contains active compounds referred to as eleutherosides A through M. The applicable part of Siberian Ginseng is the root. The eleuthrosides include a variety of diverse compounds including saponins (daucosterol, beta-stitosterol, hederasaponin B), coumarins (isofraxidin), lignans (sesamin, syringoresinol), phenylpropanoids (syringin, caffeic acid, sinapyl alcohol, coniferyl aldehyde), betulinic acid, vitamins (vitamin E), and provitamins (beta-carotene). Siberian Ginseng and its lignan constituents, sesamin and syringin, seem to have immunostimulatory effects. Several constituents are also thought to have anti-oxidant and possible anticancer effects. Several studies indicate Siberian ginseng might have protein-anabolic activity and stimulate the pituitary-adrenocortical system. Siberian ginseng may also have an estrogenic effect. Siberian Ginseng can be purchased from, Superior Trading Company, 837 Washington Street, San Francisco, Calif., 94108, 415-495-7988. Siberian Ginseng (eleutherococcus senticosus) is also known as ci wu jia, ciwujia, devil's bush, devil's shrub, eleuthera, elethero ginseng, eleutherococ, eleutherococci radix, eleutherococcus, ginseng, phytoestrogen, shigoka, Siberian ginseng, thorny bearer of free berries, touch-me-not, untouchable, wild pepper, wu jia pi, wu-jia, ussuri, and ussurian thorny pepper bush.

The present embodiments meet these needs.

SUMMARY

The present embodiments relate to an evening dose of bio-identical hormones in a solvent with a vasodilator and a hormone modulator and a carrier for balancing and maintaining Cortisol level in a human.

The embodied methods for balancing and maintaining Cortisol levels in humans. The methods involve identifying one's hormonal needs, using blood or saliva tests to ascertain the current hormonal relationship in the body, inserting the test results into a hormone tree, and balancing the hormones in a ratio that is normal for the particular person. The method continues by modifying the inserted values from the test results to account for at least one of a group of symptoms, changing the modified value to accommodate for sex type of an individual forming a gender accommodated value, and creating a formulation that priors an amount of bio-identical hormones to bring the gender accommodated value up to the normal ratio.

DETAILED DESCRIPTION OF THE EMBODIMENTS

Before explaining the present embodiments in detail, it is to be understood that the embodiments are not limited to the particular embodiments and that it can be practiced or carried out in various ways.

The present embodiments are directed to methods for balancing and maintaining Cortisol levels in humans. The methods involve identifying the hormonal needs for a human. The hormones include androdiol, andestrenedione, dehydroepiandrosterone, testosterone, estradiol, progesterone, estriol, estrone and pregnenlonone. Next, the methods includes using blood tests or saliva tests to ascertain the current relationship between the DHEA, androstenedione, testosterone and androstenediol for that human and, then, inserting the low values of each hormone level into a hormone tree. The hormone tree can include the following:

a. a ratio of pregnenolone to progesterone of 40 mg/dl to <1.5 ng/ml;

b. a ratio of progesterone to corticosterone and aldosterone of <1.5 ng/ml;

c. a ratio of progesterone to Cortisol of <1.5 ng/ml to 6-23 mcg/dl;

d. a ratio of pregnenolone to DHEA of 35-430 ug/dl to 0.7-3.1 ng/dl;

e. a ratio of DHEA to androstenedione of to 35-430 ug/dl to 0.7-3.1 ng/ml;

f. a ratio of androstenedione to testosterone of 0.7-3.1 to 6-86 ng/dl;

g. a ratio of estrone to estriol of 25-75 pg/ml to <1.2;

h. a ratio of androstenedione to testosterone 0.7-3.1 ng/ml to 6-86 ng/dl;

i. a ratio of testosterone to estradiol of 6-86 ng/dl to 25-75 pg/ml; and j. a ratio of testosterone to estriol of 6-86 ng/dl to <1.2;

The methods continue by balancing the DHEA with the androstenediol and the testosterone and the androstenediol in a ratio that is normal for the particular person and modifying the inserted values individually forming modified values. The modified values account for at least one of the following symptoms: infertility, hair loss, weight gain, depression, anxiety, panic attacks, insomnia, prostate issues, sexual enjoyment problems, irregular menstrual cycles and libido. The methods end by changing the modified value to accommodate for sex type of an individual forming a gender accommodated value and creating a formulation that priors an amount of bio-identical hormones to bring the gender accommodated value up to the normal ratio.

The present embodiments are an evening dose of bio-identical hormones in a solvent with a vasodilator and a hormone modulator and a carrier for balancing and maintaining Cortisol level in a human. The evening doses are made of progesterone in a range of 0.005-41 wt %; pregnenolone 0.005-41 wt %; ethoxydiglycol 0.005-10 wt %; pentoxifylline 0.005-10 wt %; ginseng 0.005-41 wt %, and carrier q.s.

In an alternative embodiment, the evening doses can be made of progesterone 1.65 wt %; pregnenolone 1.65 wt %; ethoxydiglycol 8.29 wt %; pentoxifylline 1.65 wt %; ginseng 3.3 wt %; and carrier q.s. The ginseng can be Siberian ginseng.

The carrier in the evening doses can be a cream, lotion, spray, gel, and enhanced oil. Ethoxydiglycol is a viscosity decreasing agent.

The evening doses can be modified for women. The evening doses modified for women are made of progesterone in a range of 1.5 to 41 wt %; ethoxydiglycol in a range of 0.005 to 10 wt %; pentoxifylline in a range of 0.005 to 10 wt %; ginseng 0.005 to 41 wt %, and a carrier q.s.

The evening doses can be modified for women who have low estrogen values. The evening dose modified for women with low estrogen values is made of progesterone in a range of 0.005-41 wt %; ethoxydiglycol 0.005-10 wt %; pentoxifylline 0.005-10 wt %; ginseng 0.005-41 wt %, and a carrier q.s.

The present embodiments are compositions that can fill individual needs for hormonal balance. The present embodiments provide a precursor to fill deficiencies in each individual's hormone balance within the common hormone tree.

An example of forming the evening dose formulations involves about five phases. The Phase A ingredients are heated at 60 degrees centigrade until melted. When the Phase A ingredients are completely melted, the Phase B ingredients are added while maintaining the 60 degree centigrade temperature. In a separate container, the first four Phase C ingredients are dissolved in the propylene glycol. When the Phase C ingredients are completely dissolved, the Phase D ingredients are added. In another separate container, the first four Phase E ingredients are dissolved in the ethoxydiglycol. Finally, the completed Phase C and Phase D and Phase E are gradually added alternately to the completed Phase A and B.

a. Phase A ingredients: sorbitan monooleate 1.5 wt %; glycerol monosterate 3.75 wt %; cetyl alcohol 2.0 wt %; stearic acid 2.0 wt %; and Peg 40 2.0 wt %;

b. Phase B ingredients: squalene 1.25 wt %; isopropyl myristate 2.2 wt %; lecithin 0.6 wt %; polysorbate 80 1.5 wt %; simethicone USP 2.0 wt %; and cyclomethicone 5.0 wt %;

c. Phase C ingredients: xanthan gum 0.5 wt %; methylparaben 0.04 wt %; propylparaben 0.02 wt %; immadiazodinyl urea 1.0 wt %; and propylene glyco 12.0 wt %;

d. Phase D ingredients: sodium hydroxide 1.9 wt %; and water 50.48 wt %; and e. Phase E ingredients: ethoxydiglycol 8.29 wt %; progesterone 1.65 wt %; pegnenolone 1.65 wt %; pentoxifylline 1.65 wt %; and ginseng 3.3 wt %.

The viscosity of the evening doses can be adjusted by varying different range percentages of the waxes. The waxes include stearic acid, cetyl alcohol, PEG 40, and similar such compounds. In order to adjust the viscosity, the different percentages of the waxes range from 0.20% to 10.0%. The viscosity of the evening dose can be further adjusted by varying the pH in different percentages of Sodium Hydroxide in ranges of 10.0% to 60.0%.

Some men and women have naturally higher levels of progesterone a gender, wherein the depletion of the hormone causes more problems. Men have far substantially lower naturally occurring levels as their gender specific base, therefore fewer male related cases of deficiency exist. At the point of progesterone deficiency, estrogen can become dominant, thereby creating estrogen dominance symptoms, such as nervousness, headaches, irritability and insomnia.

An alternative evening formulation can be Progesterone 1.65 wt/%; Pregnenolone 1.65 wt/%; Ethoxy Diglycol 8.29 wt/%; Pentoxyphillane 1.65 wt/%; Fragrance 0.04 wt/%; Ginseng 3.3 wt/%; and Cream Base 82.9 wt/%.

By allowing the body to adjust the Cortisol levels in the morning and the evening using hormones, humans and animals can cope with stress, therefore maintaining and strengthening the immune system. The bio-identical hormones usable in the present formulations and methods can be plant-based or synthetic-based hormones. The present formulations are contemplated for use in humans, horses and similar mammals.

While only a few embodiments have been disclosed in the above detailed description, the embodiments are not limited thereto, but are susceptible to various changes without departing from the scope of the invention.

While these embodiments have been described with emphasis on the embodiments, it should be understood that within the scope of the appended claims, the embodiments might be practiced other than as specifically described herein.

What is claimed is:

1. An evening dose of bio-identical hormones in a solvent with a vasodilator, a hormone modulator, and a carrier for balancing and maintaining cortisol level in a human, wherein the evening dose comprises:
    a. progesterone ranging from 0.005 wt % to 41 wt %;
    b. pregnenolone ranging from 0.005 wt % to 41 wt %;
    c. ethoxydiglycol ranging from 0.005 wt % to 10 wt %;
    d. pentoxifylline ranging from 0.005 wt % to 10 wt %;
    e. ginseng ranging from 0.005 wt % to 41 wt %, and
    f. carrier q.s.

2. The evening dose of claim 1, comprising:
    1.65 wt % of progesterone;
    1.65 wt % of pregnenolone;
    8.29 wt % of ethoxydiglycol;
    1.65 wt % of pentoxifylline;
    3.3 wt % of ginseng; and
    carrier q.s.

3. The evening dose of claim 1, wherein the ginseng is Siberian ginseng.

4. The evening dose of claim 1, wherein the carrier is selected from the group consisting of creams, lotions, sprays, gels, and enhanced oils.

5. The evening dose of claim 1, comprising:
    a. progesterone ranging from 1.5 wt % to 41 wt %;
    b. ethoxydiglycol ranging from 0.005 wt % to 10 wt %;
    c. pentoxifylline ranging from 0.005 wt % to 10 wt %;
    d. ginseng ranging from 0.005 wt % to 41 wt %; and
    e. a carrier q.s.;
    wherein the evening dose is adapted for use in women.

6. The evening dose of claim 1, comprising:
    a. progesterone ranging from 0.005 wt % to 41 wt %;
    b. ethoxydiglycol ranging from 0.005 wt % to 10 wt %;
    c. pentoxifylline ranging from 0.005 wt % to 10 wt %;
    d. ginseng ranging from 0.005 wt % to 41 wt %; and
    e. a carrier q.s.;
    wherein the evening dose is adapted for use in women with low estrogen values.

* * * * *